United States Patent [19]

Sprecker

[11] Patent Number: 4,650,603
[45] Date of Patent: Mar. 17, 1987

[54] SINGLE PHASE LIQUID MIXTURE OF TRICYCLIC ISOCHROMAN DERIVATIVE MIXTURE AND ACETYL TETRAHYDRONAPHTHALENE DERIVATIVE MIXTURE

[75] Inventor: Mark A. Sprecker, Sea Bright, N.J.

[73] Assignee: International Flavors & Fragrances Inc., New York, N.Y.

[21] Appl. No.: 759,367

[22] Filed: Jul. 26, 1985

[51] Int. Cl.$^4$ .............................................. C11B 9/00
[52] U.S. Cl. ........................... 252/522 R; 252/174.11; 252/182; 252/522 A
[58] Field of Search .......... 252/522 R, 174.11, 522 A, 252/182

[56] References Cited

U.S. PATENT DOCUMENTS 4,162,256  7/1979  Sprecker et al. ............ 252/522 R X
4,493,790  1/1985  Sprecker et al. ................ 252/522 R

OTHER PUBLICATIONS

Moelwyn–Hughes, Physical Chemistry (1961) 1058–1059.

Primary Examiner—Bernard Helfin
Attorney, Agent, or Firm—Arthur L. Liberman

[57] ABSTRACT

Described is a liquid mixture of a tricyclic isochroman derivatives and acetyl tetrahydronaphthalene derivatives wherein the acetylated tetrahydronaphthalene derivative mixture consists essentially of the compound having the structure:

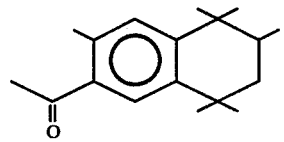

with minor amounts of compounds having the structures:

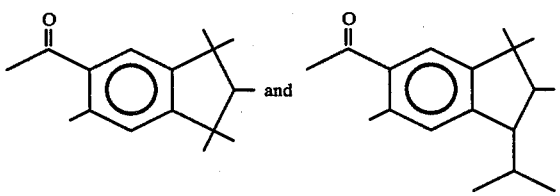

and uses of such mixtures of tricyclic isochroman derivative mixtures and acetyl tetrahydronaphthalene derivative mixtures in augmenting or enhancing the aroma of perfume compositions, colognes and perfumed articles including but not limited to solid or liquid anionic, cationic, nonionic or zwitterionic detergents, fabric softener compositions, fabric softener articles, hair preparations, cosmetic powders and perfumed polymers.

4 Claims, 7 Drawing Figures

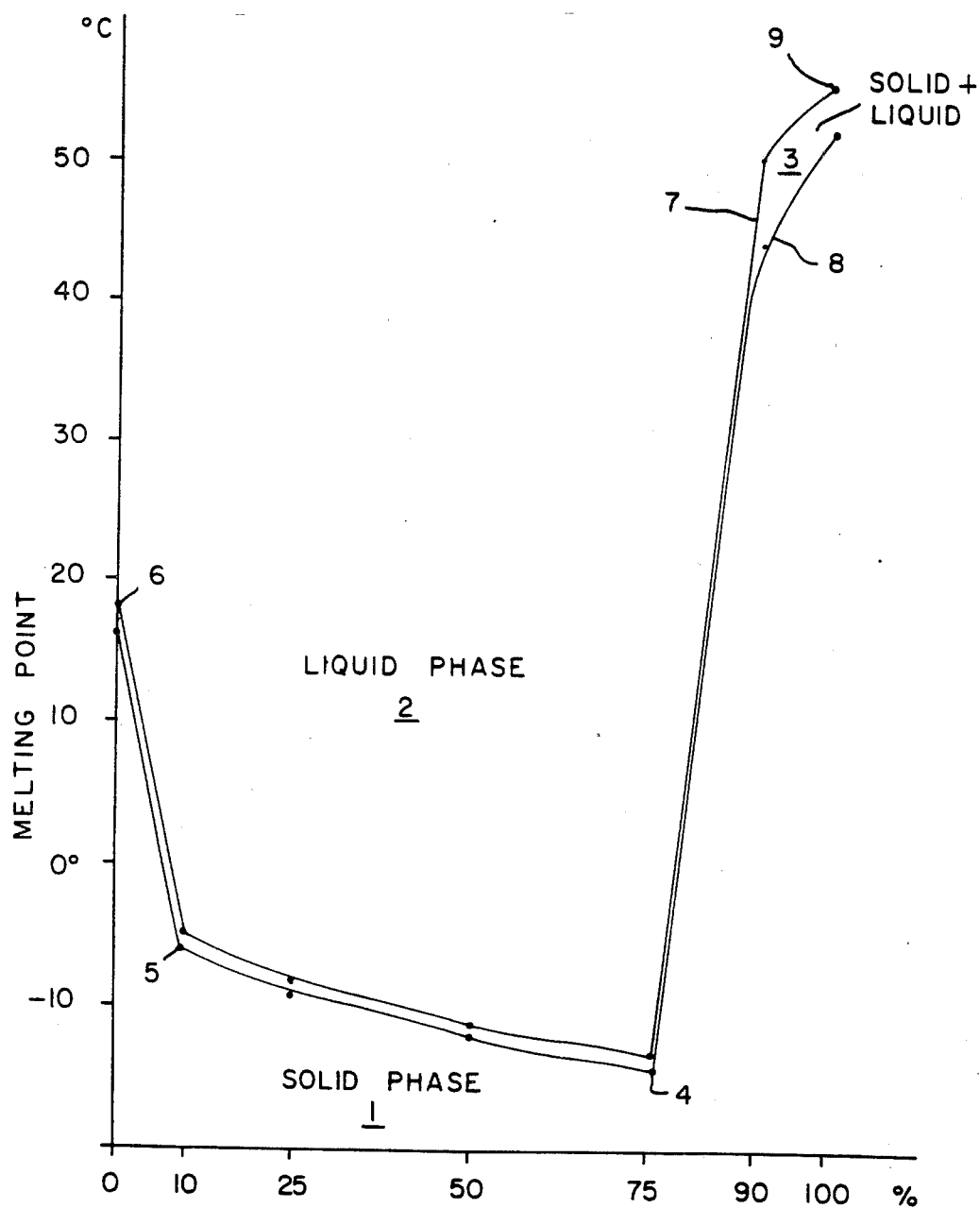

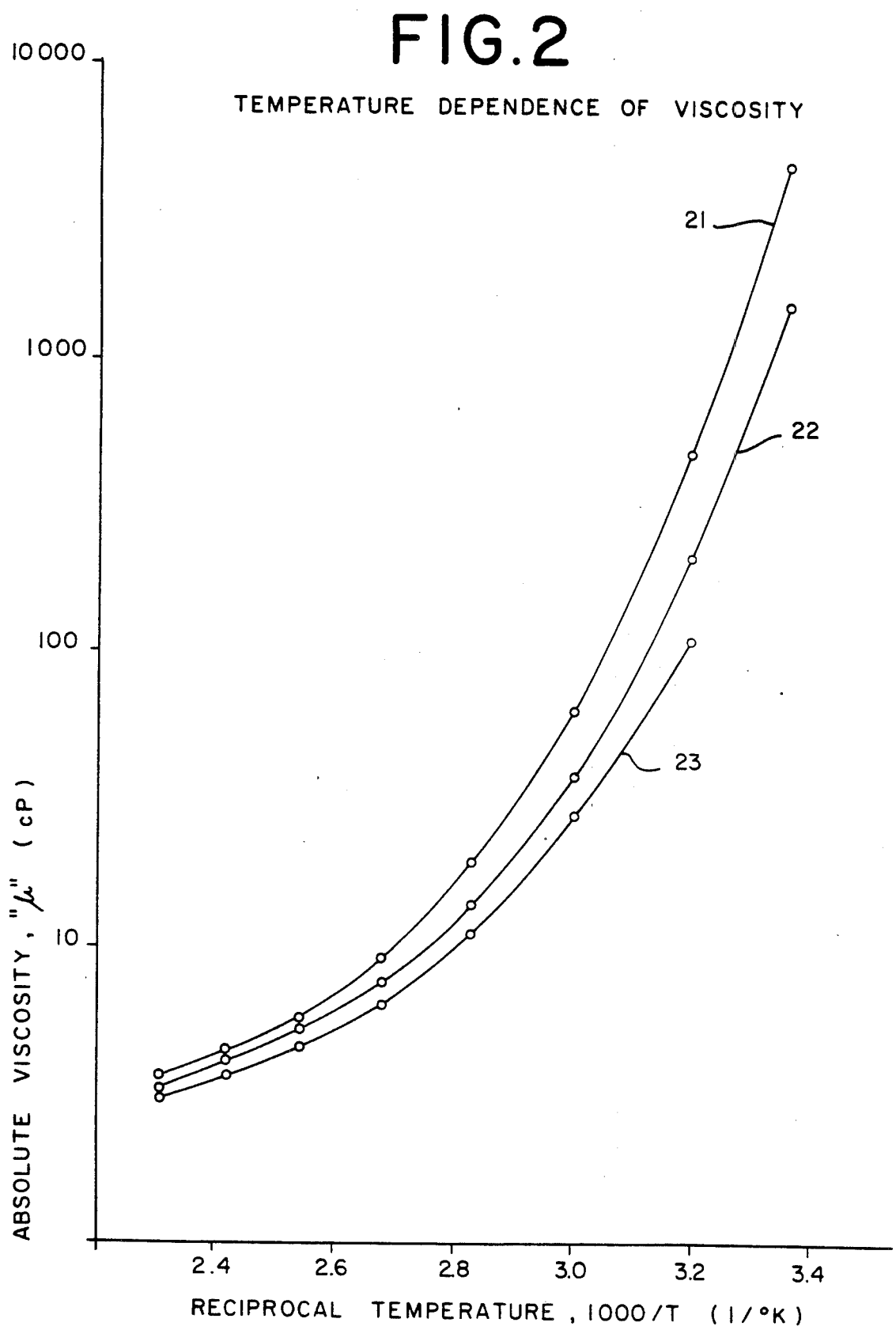

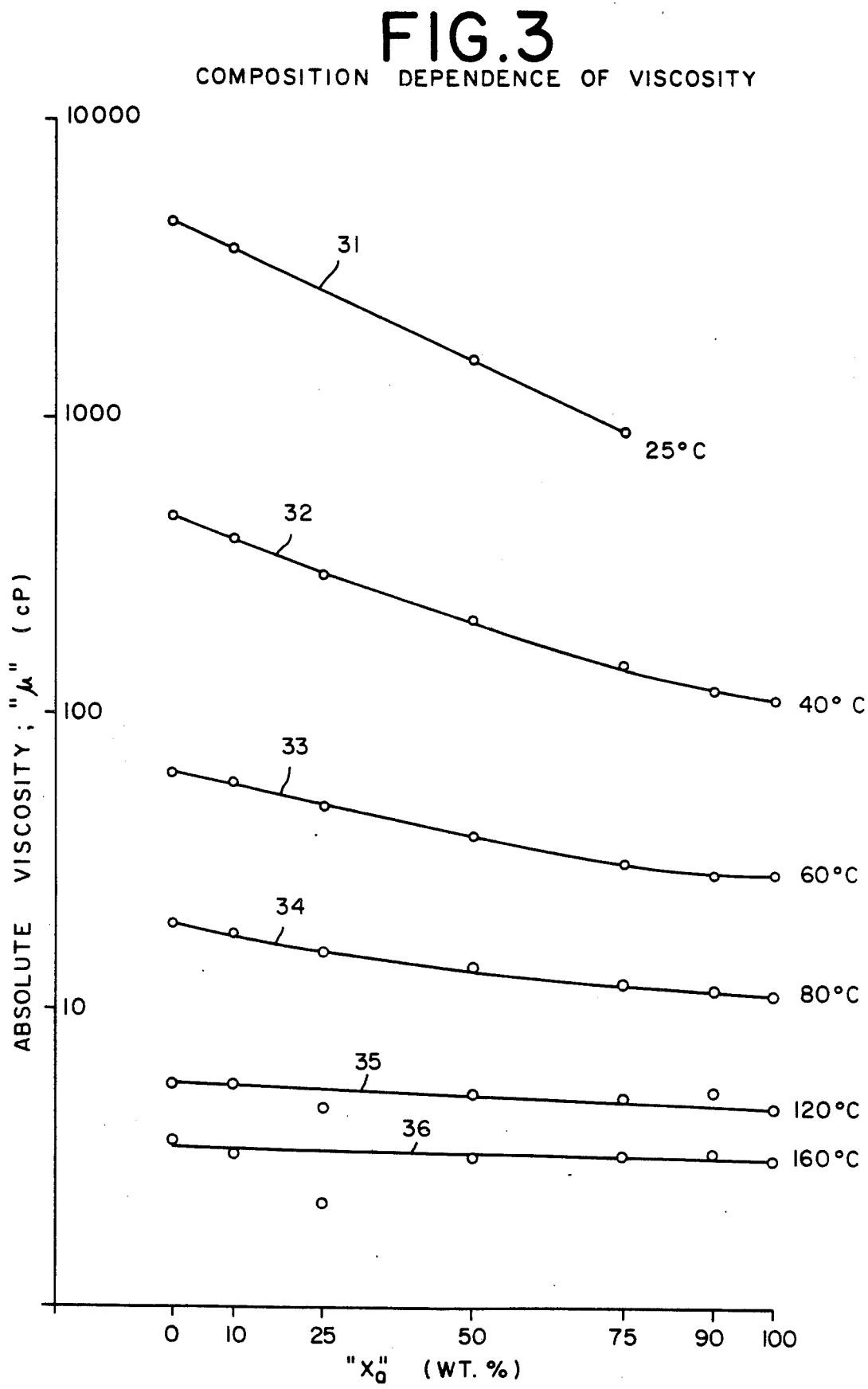

GLC PROFILE

GLC PROFILE

SINGLE PHASE LIQUID MIXTURE OF TRICYCLIC ISOCHROMAN DERIVATIVE MIXTURE AND ACETYL TETRAHYDRONAPHTHALENE DERIVATIVE MIXTURE

BACKGROUND OF THE INVENTION

The present invention relates to a liquid phase mixture of tricyclic isochroman derivative mixtures and acetyl tetrahydronaphthalene derivative mixtures as well as organoleptic uses thereof to alter, modify, augment, enhance or impart aromas in (to) consumable materials.

There has been considerable work performed relating to substances which can be used to impart (to alter, modify or enhance) fragrances to (or in) various consumable materials. These substances are used to diminish the use of natural materials some of which may be in short supply and to provide more uniform properties in the finished product. Musky aromas are highly desirable in several types of perfume compositions and for use in perfumed articles. Some of the most desirable musk type compounds are normally in the solid state at room temperature. Thus, for example, the compound having the structure:

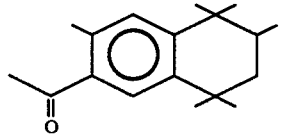

in 95% purity contains about 4% of the compound having the structure:

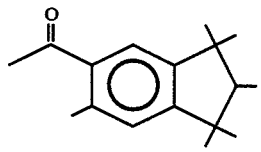

and about 1% of the compound having the structure:

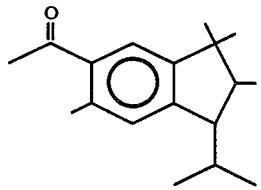

is a solid and has a melting point of between 52° C. and 56° C. at atmospheric pressure. In addition, the compound having the structure:

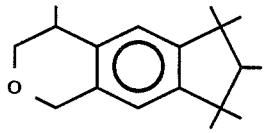

exists in pure form as a crystalline solid and is known as "GALAXOLIDE®-100". In 70–80% purity "GALAXOLIDE®" contains about 6–8% of the compounds having the structures:

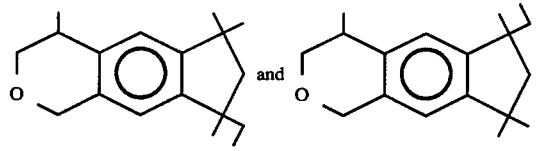

about 2–4% of the compound having the structure:

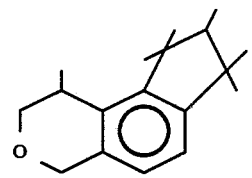

and about 2–4% of the compound having the structure:

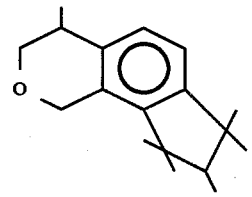

and is a highly viscous liquid at room temperature (viscosity, 4500 centipoises at 25° C.). Such material is hereinafter referred to simply as "GALAXOLIDE®". The fact that the acetyl tetrahydronaphthalene derivative mixture as defined, supra is in the solid state and the fact that the isochroman derivative mixture, "GALAXOLIDE®" is a highly viscous liquid, creates a situation which requires them (on an "individual" basis) to be utilized with diluents which cause these materials to be very difficult to work with in perfumery. Thus, as separate ingredients it is difficult to mix these materials with other perfume ingredients, and when diluted with such diluents as diethyl phthalate and the like the diluents restrict the use of the overall materials as a result of the aroma nuances which are contributed by the diluents even though such aroma nuances may not contribute very much to the overall organoleptic profile of the resulting perfume, cologne or perfumed article.

A process for the production of isochromans useful in my invention has been shown in the prior art and certain novel isochromans have recently been disclosed with outstanding musk fragrances. Such isochromans have been disclosed in Heeringa and Beets, U.S. Pat. No. 3,360,530 issued on Dec. 26, 1967 and in Wiegers, et al, U.S. Pat. No. 4,295,978 issued on Oct. 20, 1981. In addition, several other references set forth processes for production of isochromans such as U.S. Pat. No. 3,532,719, U.S. Pat. No. 3,910,964 as well as U.S. Pat. No. 3,978,090.

Although eutectic compositions of organic compounds are known to exist as is set forth in U.S. Pat. No. 3,948,914 issued on Mar. 3, 1970, eutectic mixtures of tricyclic isochroman derivative mixtures and acetyl tetrahydronaphthalene derivative mixtures as are disclosed in the instant application are unknown and furthermore, eutectic mixtures are unknown for use in perfumery.

BRIEF DESCRIPTION OF THE DRAWINGS

FIG. 1 is a phase diagram plotting melting point in degrees centigrade versus percent of "acetyl tetrahydronaphthalene derivative mixture" in the mixture (this "acetyl tetrahydronaphthalene derivative is a mixture containing 95% of the compound having the structure:

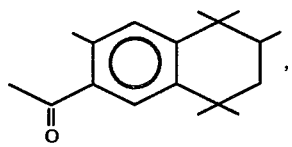

about 4% of the compound having the structure:

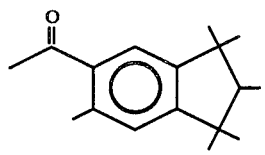

and about 1% or less of the compound having the structure:

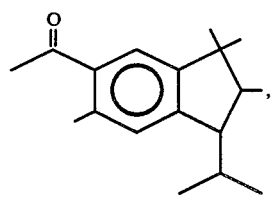

The other part of the mixture is "GALAXOLIDE ®" which is a mixture of compounds containing 70–80% of the compound having the structure:

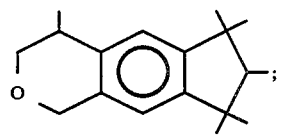

6–8% of the compounds having the structures:

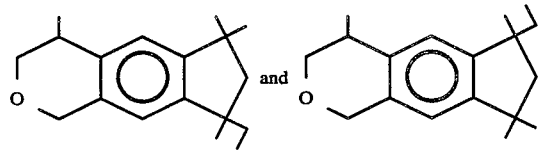

2–4% of the compounds having the structure:

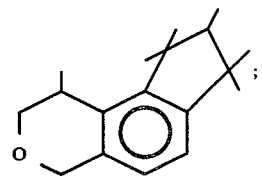

and 2–4% of the compound having the structure:

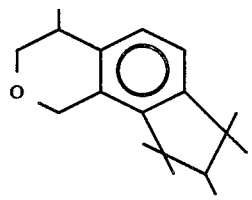

FIG. 2 is a plot of viscosity in centipoises versus reciprocal temperature (in degrees Kelvin$^{-1} \times 10^3$) for three mixtures: (a) 100% "GALAXOLIDE ®" (b) 50% "GALAXOLIDE ®" and 50% acetyl tetrahydronaphthalene derivative mixture and (c) 100% acetyl tetrahydronaphthalene derivative mixture, as defined in the description of FIG. 1, supra.

FIG. 3 is a plot of absolute viscosity in centipoises versus percent acetyl tetrahydronaphthalene derivative mixture in the mixture of tricyclic isochroman derivative mixture and acetyl tetrahydronaphthalene derivative mixture, with various temperature parameters from 25° C. up to 160° C.

Figure 4:
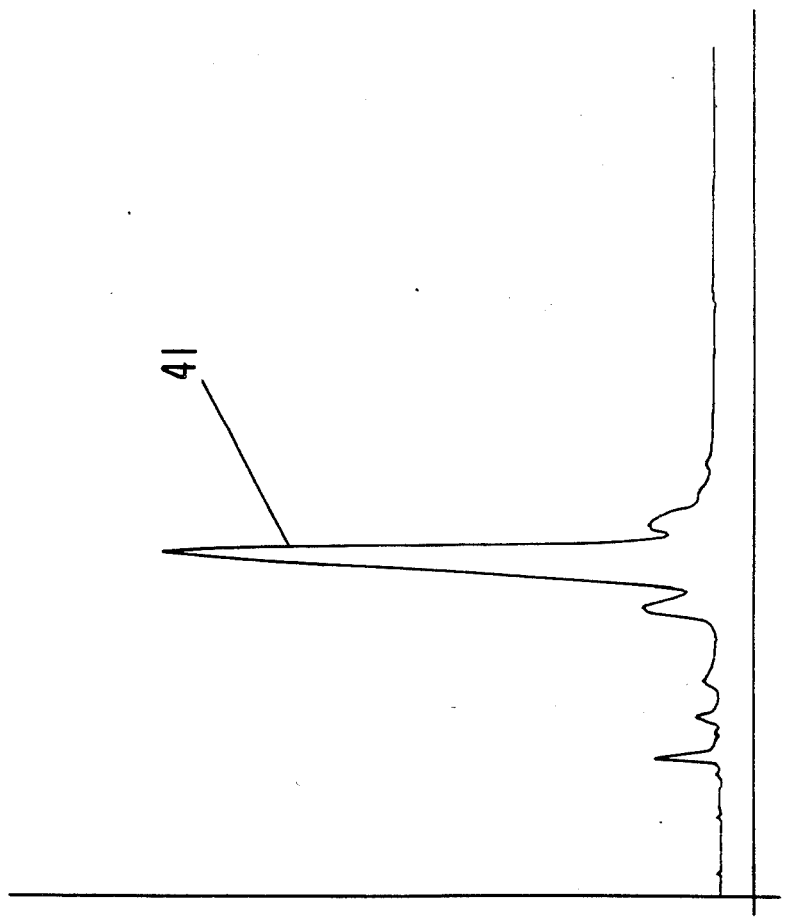

FIG. 4 is the GLC profile for the mixture of "GALAXOLIDE ®" and acetyl tetrahydronaphthalene derivative mixture, to wit: 10% acetyl trahydronaphthalene derivative mixture and 90% "GALAXOLIDE ®" (Conditions: 10'×0.125" SE-30 column programmed at 220° C. isothermal).

Figure 5:
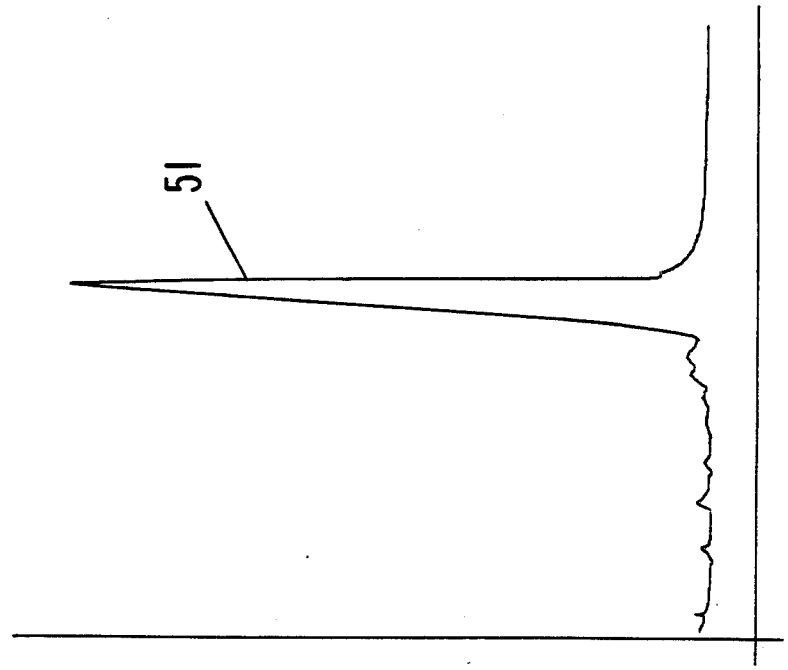

FIG. 5 is the GLC profile for a mixture containing 75% acetyl tetrahydronaphthalene derivative mixture and 25% "GALAXOLIDE ®" (Conditions: 10'×0.125" SE-30 column programmed at 220° C. isothermal).

Figure 6:
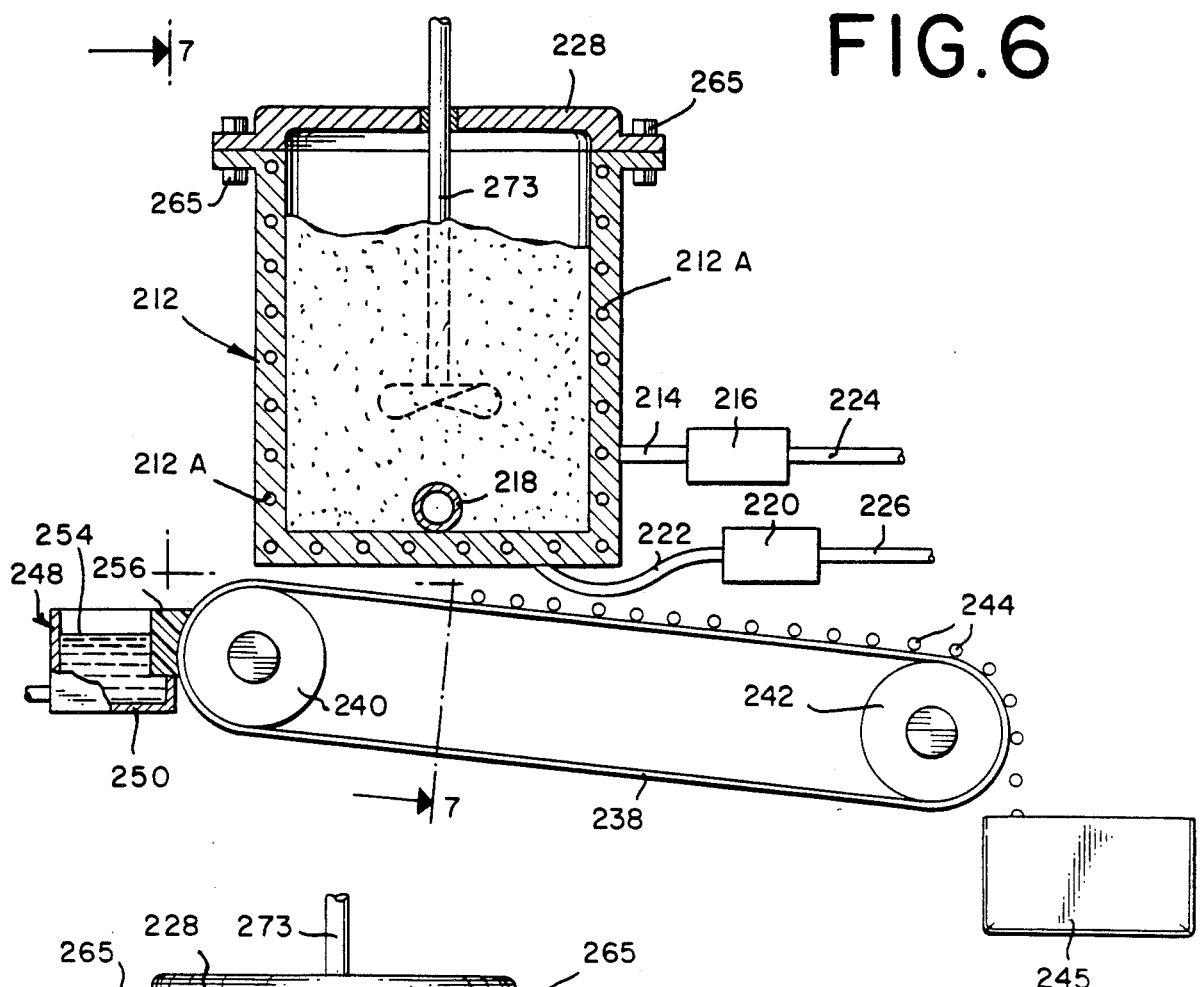

FIG. 6 represents a cut-away side elevation view of apparatus used in forming perfumed polymers containing a liquid single phase mixture of tricyclic isochroman derivative mixture and acetyl tetrahydronaphthalene derivative mixture of my invention.

Figure 7:
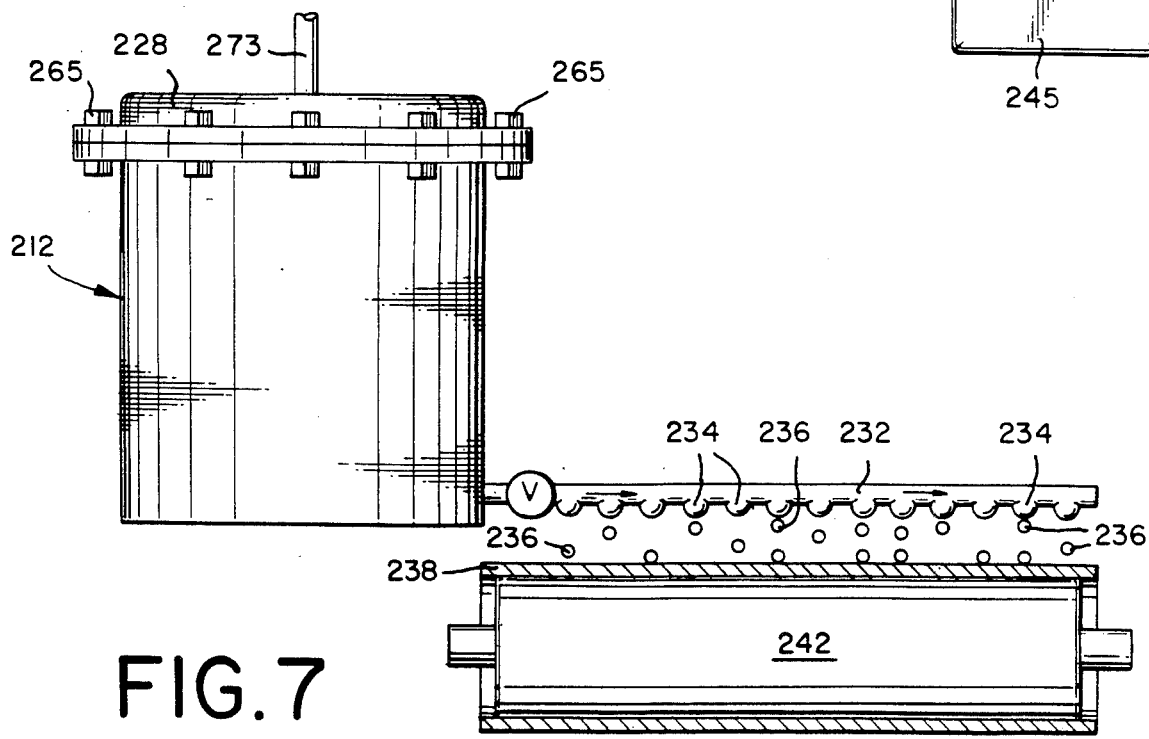

FIG. 7 is a front view of the apparatus of FIG. 6 looking in the direction of the arrows.

DETAILED DESCRIPTION OF THE DRAWINGS

FIG. 1 is a plot showing melting point in degrees centigrade versus percent acetyl tetrahydronaphthalene derivative mixture in the mixture of acetyl tetrahydronaphthalene derivative mixture and "GALAXOLIDE ®". The area of the curve indicated by reference numeral 2 is the area in which a liquid phase exists. The area of the plot indicated by reference numeral 1 is the area where a solid phase exists. The area between curves 7 and 8 and indicated by reference numeral 3 is the area of the plot where a mixture of solid and liquid exists . . . three phases, two solid and one liquid phase. It is noteworthy that at that location on the plot indicated by reference numeral 6, the melting point of "GALAXOLIDE ®" (between 17° and 19° C.) is indicated and at location 9 of the melting point of acetyl tetrahydronaphthalene derivative mixture is indicated (52°–54° C.). When the acetyl tetrahydronaphthalene derivative mixture is added to the "GALAXOLIDE ®", even as low as 10% acetyl tetrahydronaphthalene derivative mixture creates a rather significant reduction in the melting point of the mixture . . . down to about −8° C. Continued addition of acetyl tetrahydronaphthalene derivative mixture to the overall mixture up to 75% reduces the melting point down to the eutectic range of from −13° C. down to −14° C. as indicated at reference numeral 4. The mixture of from 10% up to 75% acetyl tetrahydronaphthalene derivative mixture and from 25% up to 90% "GALAXOLIDE ®" is representative of the mixtures of my invention.

FIG. 2 is a plot of absolute viscosity in centipoises versus reciprocal temperature in degrees Kelvin$^{-1} \times 10^{+3}$. As the temperature decreases the reciprocal temperature increases. As the temperature decreases the absolute viscosity increases. The curve showing the relationship of absolute viscosity to reciprocal temperature for 100% "GALAXOLIDE ®" is indicated by reference numeral 21. The curve indicating the relationship of absolute viscosity versus reciprocal temperature for the mixture of 50% "GALAXOLIDE ®" and 50% acetyl tetrahydronaphthalene derivative mixture is indicated by the reference numeral 22. The curve indicating the relationship of absolute viscosity to reciprocal temperature for 100% acetyl tetrahydronaphthalene derivative mixture is indicated by reference numeral 23.

FIG. 3 is a plot of absolute viscosity in centipoises versus percent acetyl tetrahydronaphthalene derivative mixture in the overall mixture of acetyl tetrahydronaphthalene derivative mixture and "GALAXOLIDE ®" for various temperatures. The curve indicated by reference numeral 31 is the curve indicating the relationship of absolute viscosity to percent acetyl tetrahydronaphthalene derivative mixture at 25° C. The curve indicated by reference numeral 32 is the curve showing the relationship of absolute viscosity to percent acetyl tetrahydronaphthalene derivative mixture at 40° C. The curve indicated by reference numeral 33 is the curve showing the relationship of absolute viscosity and percent acetyl tetrahydronaphthalene derivative mixture at 60° C. The curve indicated by reference numeral 34 is the curve indicating the relationship of absolute viscosity and percent acetyl tetrahydronaphthalene derivative mixture at 80° C. The curve indicated by reference numeral 35 shows the relationship of absolute viscosity and percent acetyl tetrahydronaphthalene derivative mixture at 12° C. The curve indicated by reference numeral 36 is the curve showing the relationship of absolute viscosity to percent acetyl tetrahydronaphthalene derivative mixture at 160° C. In all cases but most dramatically at about room temperature the viscosity of the "GALAXOLIDE ®" decreases substantially as acetyl tetrahydronaphthalene derivative mixture, solid in its pure form is added to the highly viscous "GALAXOLIDE ®". This reduction in viscosity is unexpected, advantageous and unobvious.

FIG. 4 is the GLC profile for a mixture of 10% acetyl tetrahydronaphthalene derivative mixture and 90% "GALAXOLIDE ®" (conditions: 10′×0.125″ SE-30 column programmed at 220° C. isothermal). The peak indicated by reference numeral 41 is the peak for the mixture of 10% acetyl tetrahydronaphthalene derivative mixture and 90% "GALAXOLIDE ®". It is a unitary GLC peak.

FIG. 5 is the GLC profile for a mixture of 75% acetyl tetrahydronaphthalene derivative mixture and 25% "GALAXOLIDE ®" (conditions: 10′×0.125″ SE-30 column programmed at 220° C. isothermal). The peak indicated by reference numeral 51 is the peak for the liquid mixture of 75% acetyl tetrahydronaphthalene derivative mixture and "GALAXOLIDE ®".

Referring to FIGS. 6 and 7, there is provided a process for forming scented polymer elements (wherein the polymer may be a thermoplastic polymer such as low density polyethylene or polypropylene or copolymers of ethylene-vinyl acetate or mixtures of a polymer and copolymer such as a copolymer of ethylene-vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower-most portion of the container is maintained at a slightly lower temperature and the material of the container is taken off at such location for delivery through the conduit. Thus, referring to FIGS. 6 and 7, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken along or in admixture with other copolymers and a perfuming substance containing the liquid mixture of tricyclic isochroman derivative mixture and acetyl tetrahydronaphthalene derivative mixture of my invention is placed. The container is closed by means of an air-tight lid 228 and clamped to the container by bolts 265. A stirrer 273 traverses the lid or cover 228 in an air-tight manner and is rotatable in a suitable manner. A surrounding cyclinder 212A having heated coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within a temperature range of, for example, 250° C. in the case of low density polyethylene. The bottom portion of the container 212 is heated by means of heating coils 212A regulated through the control 220 connected thereto through a connecting wire 222 to maintain the lower portion of the container 212 with a temperature range of 225°–240° C.

Thus, the polymer or mixture of polymers added to the container 212 is heated from 10–12 hours, whereafter the perfume composition or perfume material containing the liquid mixture of tricyclic isochroman derivative mixture and acetyl tetrahydro-naphthalene derivative mixture of my invention is quickly added to the melt. Generally, about 10–45 percent by weight of the resulting mixture of the perfumery substance is added to the polymer.

After the perfume material is added to the container 212 the mixture is stirred for a few minutes, for example, 5–15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer intimately admixed with the perfume substance containing the liquid mixture of tricyclic isochroman derivative mixture and acetyl tetrahydronaphthalene derivative mixture of my invention will continuously drop through the orifices 234 downwardly from the conduit 232. During this time, the temperature of the polymer intimately admixed with the perfumery substance in the container 212 is accurately controlled so that a temperature in the range of from about 240°–250° C. (in the case of low density polyethylene) will exist in the conduit 232. The regulation of the temperature through the control 216 and 220 is essential in order to insure temperature balance to provide for the continuous dropping or dripping of molten polymer intimately admixed with the perfume substance containing the liquid mixture of tricyclic isochroman derivative mixture and acetyl tetrahydronaphthalene derivative mixture of my invention through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for formation of other functional products, e.g., garbage bags and the like.

SUMMARY OF THE INVENTION

My invention relates to liquid single phase mixtures of tricyclic isochroman derivative mixtures and acetyl tetrahydronaphthalene derivative mixtures containing from 10% up to 75% of acetyl tetrahydronaphthalene derivative mixtures and from 25% up to 90% of isochroman derivative mixtures at temperatures greater than about 0° C. More specifically, my invention relates to mixtures of acetyl hexamethyl tetrahydronaphthalene derivative mixtures containing the compound having the structure:

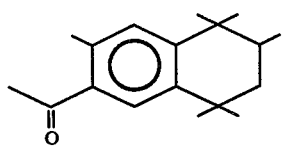

in an amount of about 95%, the compound having the structure:

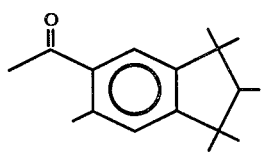

in an amount of about 4% and the compound having the structure:

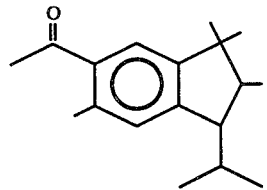

in an amount of about 1%.

in admixture with an isochroman derivative mixture containing from about 70% up to about 80% of the compound having the structure:

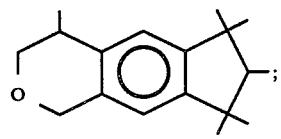

from about 6% up to about 8% of the compound having the structure:

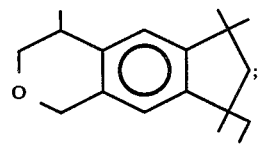

from about 6% up to about 8% of the compound having the structure:

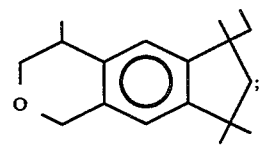

from about 2% up to about 4% of the compound having the structure:

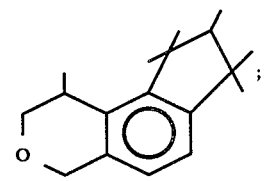

and from about 2% up to about 4% of the compound having the structure:

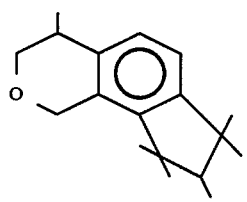

All percentages are given by weight unless otherwise indicated.

As stated, supra, a problem has existed heretofor in the formulation of perfumes containing "GALAXOLIDE®" a mixture of isochromans defined, supra containing 70%–80% of the compound having the structure:

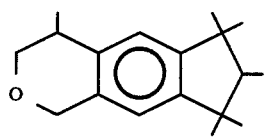

This mixture is a highly viscous liquid at room temperature. A problem has also existed in the formulation of perfumes with acetyl tetrahydronaphthalene derivative mixtures containing 95% by weight of the compound having the structure:

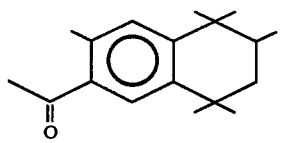

which mixture is a solid at room temperature having a melting point of 52°–54° C. Surprisingly, and unexpectedly when these two materials are mixed, (which they are in many cases in perfumery since both impart different but complimentary musk nuances in perfumery) the melting point of the mixture is substantially lowered and, in addition, the viscosity of the mixture is lowered as the percentages vary between 10% up to 75% acetyl tetrahydronaphthalene derivative mixture and from 25% up to 90% "GALAXOLIDE®".

We have further and more specifically determined that mixtures of acetyl tetrahydronaphthalene derivative mixtures containing as the main component the compound having the structure:

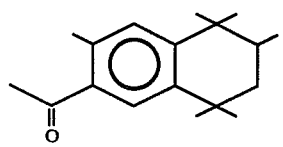

in an amount of about 95% and including the impurities having the structure:

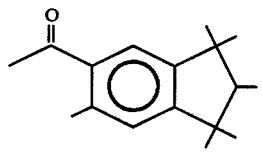

(in an amount of about 4% and the compound having the structure:

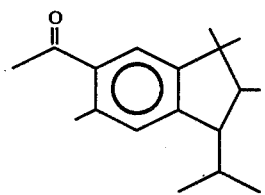

in an amount of about 1%) and "GALAXOLIDE®" having the structure:

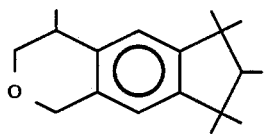

(in an amount of from about 70% up to about 80%) containing the impurities, to wit:
(a) the compound having the structure:

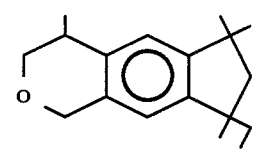

in an amount of from about 6–8%;
(b) the compound having the structure:

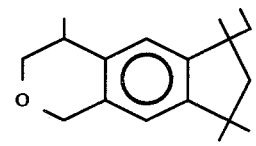

in an amount of from about 6% up to about 8%;
(c) the compound having the structure:

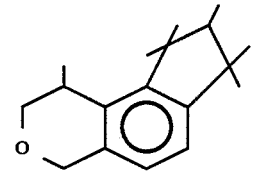

in an amount of from about 2% up to about 4%; and
(d) the compound having the structure:

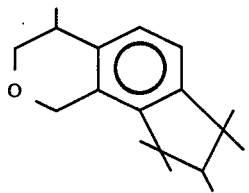

in an amount of from about 2% up to about 4% have a viscosity that can be defined according to the equations:

$$\ln \mu_M = X_G\left(A + \frac{B}{T+C}\right) + X_a\left(A' + \frac{B'}{T+C'}\right)$$

and $$X_G + X_a = 1$$

wherein $\mu_M$ is the viscosity in centiposies of the mixture of tricyclic isochroman derivative mixture and acetyl tetrahydronaphthalene derivative mixture; wherein $X_G$ is the weight percent of "GALAXOLIDE®"; wherein $X_a$ is the mixture of the weight percent of acetyl tetrahydronaphthalene derivative mixture; wherein "T" is the temperature at which the viscosity is being calculated in degrees Celsius; and wherein "A", "B", "C", "A'", "B'" and "C'" are constants necessary for the calculation based on emperical data. Thus, the constant "A" ranges from $-1.26$ up to $-1.16$. The constant "B" ranges from 413.58 up to 430.46; the constant "C"

from 236.25 up to 279.65; and the constant "C'" ranges from 9.95 up to 10.47. The constants A, B and C are obtained using regression analysis employing the Marquardt Levenburg method. The data for the various measurements is set forth in the following tables:

TABLE I

VISC_GH 9R × 6C

GALAXOLIDE VISCOSITY MEASUREMENTS

| 0 | 1 T OBS (Deg C.) | 2 Visc OBS (Cps) | 3 ln V | 4 A, B, & C | 5 Visc Antoine | 6 % Error |
|---|---|---|---|---|---|---|
| 1 | 23 | 6990.0 | 8.8522 | −1.205842 | 7297.8 | 4.4 |
| 2 | 25 | 4510.0 | 8.4141 | 422.024487 | 4600.3 | 2.0 |
| 3 | 40 | 472.5 | 6.1580 | 18.779764 | 393.0 | −16.8 |
| 4 | 60 | 63.0 | 4.1431 | | 63.0 | 0.8 |
| 5 | 80 | 19.5 | 2.9704 | | 21.5 | 10.1 |
| 6 | 100 | 9.2 | 2.2192 | | 10.6 | 13.7 |
| 7 | 120 | 5.7 | 1.7405 | | 6.3 | 9.9 |
| 8 | 140 | 4.5 | 1.5041 | | 4.3 | −5.1 |
| 9 | 160 | 3.7 | 1.3083 | | 3.2 | −14.2 |

TABLE II

VISC_AST 7R × 6C

ASTRALIDE VISCOSITY MEASUREMENTS

| 0 | 1 T OBS (Deg C.) | 2 Visc OBS (Cps) | 3 ln V | 4 A, B, & C | 5 Visc Antoine | 6 % Error |
|---|---|---|---|---|---|---|
| 1 | 40 | 108.5 | 4.6868 | −0.427431 | 111.0 | 2.3 |
| 2 | 60 | 28.0 | 3.3322 | 257.947455 | 25.7 | −8.2 |
| 3 | 80 | 11.1 | 2.4069 | 10.212873 | 11.4 | 2.5 |
| 4 | 100 | 6.3 | 1.8405 | | 6.8 | 7.5 |
| 5 | 120 | 4.6 | 1.5261 | | 4.7 | 2.8 |
| 6 | 140 | 3.7 | 1.3083 | | 3.6 | −1.8 |
| 7 | 160 | 3.1 | 1.1314 | | 3.0 | −4.2 |

TABLE III

VISC_OBS 7R × 8C

VISCOSITY (Cp) MEASUREMENTS OF GALAXOLIDE/ASTRALIDE MIXTURE

| 0 | % AST | 1 Visc @ 25 C. | 2 Visc @ 40 C. | 3 Visc @ 60 C. | 4 Visc @ 80 C. | 5 Visc @ 100 C. | 6 Visc @ 120 C. | 7 Visc @ 140 C. | 8 Visc @ 160 C. |
|---|---|---|---|---|---|---|---|---|---|
| 1 | 0% Ast | 4510 | 472.5 | 63.0 | 19.5 | 9.2 | 5.7 | 4.5 | 3.7 |
| 2 | 10% Ast | 3720 | 394.0 | 57.5 | 17.9 | 8.8 | 5.7 | 4.3 | 3.3 |
| 3 | 15% Ast | 2885 | 293.5 | 48.1 | 15.4 | 7.4 | 4.6 | 3.3 | 2.3 |
| 4 | 50% Ast | 1530 | 206.6 | 38.2 | 14.0 | 7.5 | 5.3 | 4.3 | 3.2 |
| 5 | 75% Ast | 895 | 143.3 | 31.4 | 12.1 | 7.0 | 5.1 | 3.8 | 3.3 |
| 6 | 90% Ast | — | 118.0 | 27.9 | 11.6 | 6.9 | 5.3 | 4.7 | 3.3 |
| 7 | 100% Ast | — | 108.5 | 28.0 | 11.1 | 6.3 | 4.6 | 3.7 | 3.1 |

TABLE IV

VISC_PRED 7R × 8C

VISCOSITY (Cp) PREDICTED OF GALAXOLIDE/ASTRALIDE MIXTURE

| 0 | % Ast | 1 Visc @ 25 C. | 2 Visc @ 40 C. | 3 Visc @ 60 C. | 4 Visc @ 80 C. | 5 Visc @ 100 C. | 6 Visc @ 120 C. | 7 Visc @ 140 C. | 8 Visc @ 160 C. |
|---|---|---|---|---|---|---|---|---|---|
| 1 | 0% Ast | 4600 | 393.0 | 63.5 | 21.5 | 10.5 | 6.3 | 4.3 | 3.2 |
| 2 | 10% Ast | 3945 | 346.4 | 58.0 | 20.1 | 10.0 | 6.1 | 4.2 | 3.2 |
| 3 | 15% Ast | 3654 | 325.1 | 55.4 | 19.5 | 9.8 | 6.0 | 4.2 | 3.1 |
| 4 | 50% Ast | 2134 | 208.9 | 40.4 | 15.6 | 8.4 | 5.4 | 3.9 | 3.1 |
| 5 | 75% Ast | 1454 | 152.3 | 32.2 | 13.3 | 7.6 | 5.1 | 3.8 | 3.0 |
| 6 | 90% Ast | 1155 | 126.0 | 28.1 | 12.1 | 7.1 | 4.9 | 3.7 | 3.0 |
| 7 | 100% Ast | 990 | 111.0 | 25.7 | 11.4 | 6.8 | 4.7 | 3.6 | 3.0 | ranges from 15.62 up to 21.95; the constant "A'" ranges from −0.437 up to −0.417; the constant "B'" ranges

TABLE V

VISC_OBS_PRED 7R × 8C

% ERROR OF VISCOSITY OBSERVED -VS- PREDICTED

| 0 | % Ast | 1% ERROR at 25 C. | 2% ERROR at 40 C. | 3% ERROR at 60 C. | 4% ERROR at 80 C. | 5% ERROR at 100 C. | 6% ERROR at 120 C. | 7% ERROR at 140 C. | 8% ERROR at 160 C. |
|---|---|---|---|---|---|---|---|---|---|
| 1 | 0% Ast | −2.0 | 16.8 | −0.8 | −10.3 | −14.1 | −10.5 | 4.4 | 13.5 |

TABLE V-continued

VISC__OBS__PRED 7R × 8C

| | | % ERROR OF VISCOSITY OBSERVED -VS- PREDICTED | | | | | | | |
|---|---|---|---|---|---|---|---|---|---|
| 0 | % Ast | 1% ERROR at 25 C. | 2% ERROR at 40 C. | 3% ERROR at 60 C. | 4% ERROR at 80 C. | 5% ERROR at 100 C. | 6% ERROR at 120 C. | 7% ERROR at 140 C. | 8% ERROR at 160 C. |
| 2 | 10% Ast | −6.0 | 12.1 | −0.9 | −12.3 | −13.6 | −7.0 | 2.3 | 3.0 |
| 3 | 15% Ast | −26.7 | −10.8 | −15.2 | −26.6 | −32.4 | −30.4 | −27.3 | −34.8 |
| 4 | 50% Ast | −39.5 | −1.1 | −5.8 | −11.4 | −12.0 | −1.9 | 9.3 | 3.1 |
| 5 | 75% Ast | −62.5 | −6.3 | −2.5 | −9.9 | −8.6 | 0.0 | 0.0 | 9.1 |
| 6 | 90% Ast | — | −6.8 | −0.7 | −4.3 | −2.9 | 7.5 | 21.3 | 9.1 |
| 7 | 100% Ast | — | −2.3 | 8.2 | −2.7 | −7.9 | −2.2 | 2.7 | 3.2 |

The liquid mixture of tricyclic isochroman derivative mixture and acetyl tetrahydronaphthalene derivative mixture of my invention and one or more auxiliary perfume ingredients including, for example, alcohols other than the liquid mixture of tricyclic isochroman derivative mixture and acetyl tetrahydronaphthalene derivative mixture of my invention and one or more auxiliary perfume ingredients, aldehydes, nitriles, esters, cyclic esters, ketones, ethers other than the liquid mixture of tricyclic isochroman derivative mixture and acetyl tetrahydronaphthalene derivative mixture of my invention and one or more auxiliary perfume ingredient, natural essential oils and synthetic essential oils may be admixed so that the combined odors of the individual components produce a pleasant and desired fragrance, particularly and preferably, in musk and "animal-like" fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh smelling materials.

In perfume compositions, it is the individual components which contribute to its particular olfactory characteristics, but the over-all effect of the perfume composition will be the sum of the effects of each of the ingredients. Thus, the liquid mixture of tricyclic isochroman derivative mixture and acetyl tetrahydronaphthalene derivative mixture of my invention or one or more auxiliary perfume ingredients can be used to alter the aroma characteristics of a perfume composition, for example, by utilizing or moderating the olfactory reaction contributed by at least one other ingredient in the composition.

The amount of the liquid mixture of tricyclic isochroman derivative mixture and acetyl tetrahydronaphthalene derivative mixture of my invention and one or more auxiliary perfume ingredient of my invention will be a liquid mixture of tricyclic isochroman derivative mixture and acetyl tetrahydronaphthalene derivative mixture of my invention and one or more auxiliary perfume ingredients and even less (e.g., 0.005%) can be used to impart a sweet, musk aroma for soaps, anionic, cationic and nonionic detergents, fabric softener articles and compositions of matter, cosmetics or other products. The amount employed can range up to 10% of the fragrance components and can range up to 0.5% of the weight of the perfumed article and will depend upon considerations of cost, nature of the end product, the effect desired on the finished product and the particular fragrance sought.

The liquid mixture of tricyclic isochroman derivative mixture and acetyl tetrahydronaphthalene derivative mixture of my invention and one or more auxiliary perfume ingredients are useful, taken alone or in perfume compositions as olfactory components in anionic, cationic and nonionic detergents, soaps, fabric softener compositions, fabric softener articles for use in clothes dryer (e.g., "BOUNCE ®", a registered trademark of the Proctor & Gamble Company of Cincinnati, Ohio), space odorants and deodorants, perfumes, colognes, toilet water, bath preparations, such as lacquers, brilliantines, creams, deodorants, hand lotions and sun screens; powders, such as talcs, dusting powders, face powders and the like. When used as an olfactory component in perfume compositions or perfumed article, such as anionic, cationic and nonionic detergents and in fabric softener compositions and fabric softener articles (e.g., for use in clothing dryers) as little as 0.05% of the liquid mixture of tricyclic isochroman derivative mixture and acetyl tetrahydronaphthalene derivative mixture of my invention and one or more auxiliary perfume ingredients will suffice to impart an intense sweet, musk fragrance. Generally, no more than 5% of the liquid mixture of tricyclic isochroman derivative mixture and acetyl tetrahydronaphthalene derivative mixture of our invention and one or more auxiliary perfume ingredient based on the ultimate end product is required in the perfume composition or in the perfumed article.

In addition, the perfume composition or fragrance composition of my invention can contain a vehicle or carrier for the liquid mixture of tricyclic isochroman derivative mixture and acetyl tetrahydronaphthalene derivative mixture of my invention and one or more auxiliary perfume ingredients. The vehicle can be a liquid such as a non-toxic alcohol, a non-toxic glycol, or the like. The carrier can also be an absorbent solid, such as a gum (e.g., gum arabic) or components for encapsulating the composition (such as gelatin as by means of coacervation).

It will thus be apparent that the liquid mixture of tricyclic isochroman derivative mixture and acetyl tetrahydronaphthalene derivative mixture of my invention and one or more auxiliary perfume ingredients can be utilized to alter the sensory properties, particularly organoleptic properties, such as flavors and/or fragrances of a wide variety of consumable materials.

The following examples are illustrative and the invention is to be considered restricted thereto only as indicated in the appended claims. All parts and percentages given herein are by weight unless otherwise specified.

EXAMPLE I

PREPARATION OF MIXTURE

The following mixture is prepared:

| Ingredients | Parts by Weight |
|---|---|
| A mixture of compounds having the structures: | 50 |

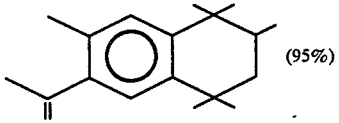 (95%)

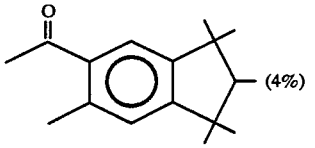 (4%)

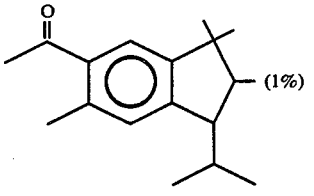 (1%)

| | |
|---|---|
| Galaxolide ®, a mixture of compounds having the structures: | 50 |

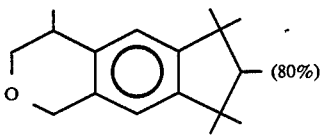 (80%)

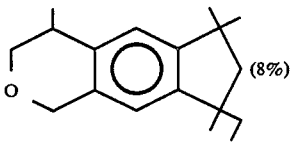 (8%)

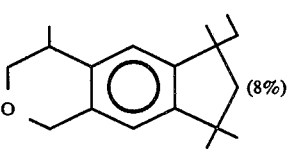 (8%)

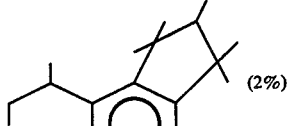 (2%)

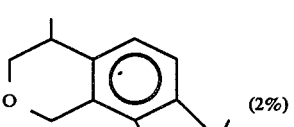 (2%)

The resulting mixture has an excellent musk aroma. The substance which is a liquid at room temperature can be blended into perfumed articles by itself without the use of additional solvent or it can be blended into other perfume compositions without the use of additional solvent as set forth in the following examples.

EXAMPLE II

MUSK PERFUME FORMULATION

The following musk perfume formulation is prepared:

| Ingredients | Parts by Weight |
|---|---|
| Musk Ambrette | 200 |
| Musk Ketone | 200 |
| Beta Ionone | 50 |
| Vetiveryl Acetate | 50 |
| Sandalwood Oil | 100 |
| Benzyl Benzoate | 400 |
| Liquid mixture of tricyclic isochroman derivative mixture and acetyl tetrahydronaphthalene derivative mixture of Example I | 20 |

The liquid mixture of tricyclic isochroman derivative mixture and acetyl tetrahydronaphthalene derivative mixture of Example I imparts to this musk formulation a natural, sweet, musk aroma with great intensity and blends in well with the formulation without any need for the use of any solvent.

EXAMPLE III

PREPARATION OF A SOAP COMPOSITION

100 Grams of soap chips are admixed with 1 gram of one of the perfume substances of Table I below until a substantially homogeneous composition is obtained. The perfumed soap manifests an excellent aroma as set forth in Table I below:

TABLE I

| Perfume Ingredients | Aroma |
|---|---|
| Liquid mixture of tricyclic isochroman derivative mixture and acetyl tetrahydronaphthalene derivative mixture of Example I. | An intense, sweet, musk aroma. |
| Perfume composition of Example II. | A natural, sweet musk aroma with great intensity. |

EXAMPLE IV

PREPARATION OF A COLOGNE AND HANDKERCHIEF PERFUME

One of the perfume substances are set forth in Table I of Example III is incorporated into a cologne at concentrations of 1.5%, 2.0%, 2.5%, 3.0%, 3.5% and 4.0% in 80%, 85%, 90% and 95% aqueous ethanol; and into handkerchief perfumes at concentrations of 15%, 20%, 25% and 30% (in 85%, 90% and 95% aqueous ethanol). Distinct and definite fragrances as set forth in Table I of Example III are imparted to the cologne and to the handkerchief perfume at each of the levels indicated.

EXAMPLE V

PREPARATION OF A COSMETIC POWDER COMPOSITION

A cosmetic powder is prepared by mixing in a ball mill, 100 grams of talcum powder with 0.15 grams of one of the substances of Table I of Example III. The resulting powders have excellent sweet musk aromas.

EXAMPLE VI

Utilizing the procedure of Example I of column 15 of U.S. Pat. No. 3,632,396 the specification for which is incorporated by reference herein, a non-woven cloth substrate useful as a dryer-added fabric-softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.);
   57 percent $C_{20-22}$ HAPS
   27 percent isopropyl alcohol
   20 percent antistatic agent
   1 percent of one of the perfume substances of Table I of Example III.

Fabric-softening compositions prepared as set froth above having an aroma characteristic as set forth in Table I of Example III essentially consists of a substrate having a weight of about 3 grams per 100 square inches, a substrate coating of about 1.85 grams per 100 square inches of substrate and an outer coating of about 1.4 grams per 100 square inches of substrate thereby providing a total aromatized substrate and an outer coating weight ratio of about 1:1 by weight of the substrate. Aromas are imparted as set forth in Table I of Example III in a pleasant manner to the head space in the dryer on operation thereof using the said dryer added fabric softening non-woven fabric.

EXAMPLE VII

PREPARATION OF A SOAP COMPOSITION

100 Grams of soap chips are prepared according to Example V of U.S. Pat. No. 4,058,490 issued on Nov. 15, 1977 the specification for which is incorporated herein by reference, as follows:

"The sodium salt of an equal mixture of $C_{10}$–$C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is dried. The resulting solid actives are then blended in a chip mixer with 10 lbs. water 0.2 lb. titanium hydroxide."

The resulting blend is then mixed with one of the perfume substances of Table I of Example III until a substantially homogeneous composition is obtained. The perfumed soap composition manifests an aroma as set forth in Table I of Example III.

EXAMPLE VIII

GRANULAR DETERGENT COMPOSITION

A granular detergent composition is prepared according to United Kingdom Pat. No. 1,501,498 the specification for which is incorporated by reference herein having the following formula. It is prepared by spray-drying the following mixture:

| Ingredient | Parts by Weight |
|---|---|
| Sodium salt of ethoxylated fatty alcohol sulfate having an average of about 2.25 moles of ethylene | 14.1 |

| Ingredient | Parts by Weight |
|---|---|
| oxide per mole of fatty alcohol | |
| Sodium tallow alkyl sulfate | 2.4 |
| Sodium silicate solids ratio: $SiO_2/Na_2O = 2.0$ | 6.0 |
| Sodium tripolyphosphate | 24.0 |
| $Na_{12}(AlO_2.SiO_2).27H_2O$ | 18.0 |
| Moisture | 10.0 |
| Sodium sulfate | 25.0 |
| Perfume substance of Table I of Example III | 4.0 |

Laundry solutions containing the above detergent compositions are used to launder fabrics. Each of the laundry compositions both prior to and on laundering give rise to a pleasant aroma as set forth in Table I of Example III.

EXAMPLE IX

PERFUMED LIQUID DETERGENT

Concentrated liquid detergents are prepared with aromas as set forth in Table I of Example III containing 0.10%, 0.15% and 0.20% of each of the substances of Table I of Example III in the liquid detergent. The liquid detergent is a builder free liquid detergent consisting of (a) 50% of a nonionic surfactant having an HLB of 8.0 and a critical micelle concentration of 0.007 weight percent at 25° C.; (b) an anionic surfactant which is a triethanolamine prepared according to United Kingdom Pat. No. 1,491,603 the specification for which is incorporated by reference herein.

The detergents all possess aromas as set forth in Table I of Example III, supra.

EXAMPLE X

PREPARATION OF A DETERGENT COMPOSITION

A total of 100 grams of detergent powder (a low phosphate content detergent composition which contains 12% by weight phosphate builder, 8 percent hardness mineral ion insensitive detergent, 0.9 percent by weight maleic anhydride-vinyl compound co-polymer and 2 percent alkylene oxide condensation product prepared according to Example IV at column IX, U.S. Pat. No. 4,000,080 issued on Dec. 28, 1976, the specification for which is incorporated by reference herein) is intimately admixed with 0.15 grams of one of the perfume materials of Table II of Example V, supra, until a substantially homogeneous composition is obtained. The composition has an aroma as set forth in Table II of Example V, supra.

EXAMPLE XI

Each of the fragranced materials of Table I of Example III, supra are added to a 50:50 weight:weight mixture of low density polyethylene:polyepsilon caprolactone PCL-700 forming pellets with scents as set forth in Table I of Example III, supra, 75 Pounds of a mixture of PCL-700 polyepsilon caprolactone (manufactured by the Union Carbide Corporation of New York, N.Y. having a melting point of about 180°–190° F.): Low density polyethylene are heated to about 250° C. in a container of the kind illustrated in FIGS. 6 and 7. 25 Pounds of each of the fragrance materials as set forth in Table I of Example III is then quickly added to the liquified polymer mixture, the lid 228 is put in place and the agitating means 273 are actuated. The temperature is then raised to about 260° F. and the mixing is continued for 5–15 minutes. The valve "V" is then opened to allow flow of the molten polymer enriched with perfume ingredient to exit through the orifices 234. The liquid falling through the orifices 234 solidifies almost instantaneously upon impact with the moving cooled conveyor 238. Polymer beads or pellets 244 having pronounced scents as described in Table I of Example III, supra are thus formed. Analysis demonstrates that the pellets contain about 25% of the perfume material so that almost no losses in the scenting substance did occur. These pellets may be called "master pellets".

50 Pounds of each batch of the scent containing "master pellets" are then added to one thousand pounds of unscented polypropylene and the mass is heated to the liquid state. The liquid is molded into thin sheets of films. The thin sheets of films have pronounced aromas as set forth in Table I of Example III, supra. The sheets of films are cut into strips of 0.25" in width×3" in length and placed into room air fresheners.

On operation of the room air freshener, after four minutes, the room in each case has an aesthetically pleasing aroma with no foul odor being present, the aroma being described in Table I of Example III, supra.

What is claimed is:

1. A liquid single phase eutectic mixture containing from 10% up to 75% by weight of an acetyl tetrahydronaphthalene derivative mixture and from 25% up to 90% by weight of an isochroman derivative mixture at a temperature greater than about 0° C. wherein said acetyl tetrahydronaphthalene derivative mixture contains about 95% by weight of the compound having the structure:

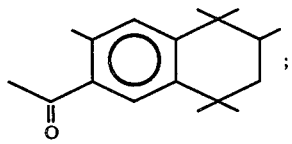

about 4% by weight of the compound having the structure:

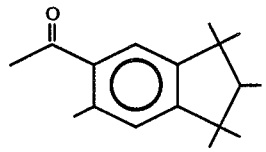

and about 1% of the compound having the structure:

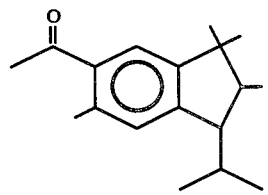

and wherein the isochroman derivative mixture contains from about 70% up to about 80% by weight of the compound having the structure:

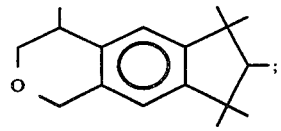

from about 6% up to about 8% of the compound having the structure:

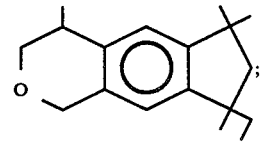

and the compound having the structure:

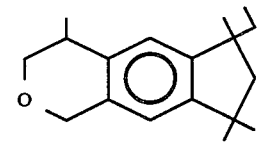

from about 2% up to about 4% of the compound having the structure:

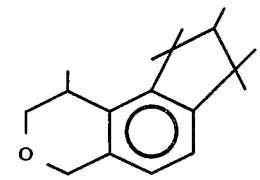

and from about 2% up to about 4% of the compound having the structure:

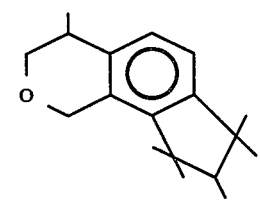

wherein the viscosity of said composition is defined according to the equations:

$$\ln \mu_M = X_G\left(A + \frac{B}{T+C}\right) + X_A\left(A' + \frac{B'}{T+C'}\right)$$

and $$X_G + X_A = 1$$

wherein $\mu_M$ represents viscosity in centipoises of the mixture; $X_G$ represents the weight fraction of the said acetyl tetrahydronaphthalene derivative mixture; $X_a$ represents the weight fraction of said tricyclic isochroman derivative mixture; T represents the temperature of the mixture in degrees Celsius; A represents a number of from −1.26 up to −1.6; B represents a number of from 413.58 up to 430.46; C represents a number of from 15.62 up to 21.95; A' represents a number of from −0.437 up to −0.417; B' represents a number of 236.25 up to 279.65; and C' represents a number of from 9.95 up to 10.47.

2. A process for augmenting or enhancing the aroma of a perfume composition comprising the step of adding to said perfume composition an aroma augmenting or enhancing quantity of the composition of matter defined according to claim 1.

3. A process for augmenting or enhancing the aroma of a liquid anionic, cationic, nonionic or zwitterionic detergent comprising the step of intimately admixing with said liquid anionic, cationic, nonionic or zwitterionic detergent an aroma augmenting or enhancing quantity of the composition of matter of claim 1.

4. A process of augmenting or enhancing the aroma of a thermoplastic polymer comprising the step of intimately admixing with said thermoplastic polymer in the liquid state an aroma augmenting or enhancing quantity of the composition of matter defined according to claim 1.

* * * * *